US00RE34964E

United States Patent [19]

Okazaki

[11] E Patent Number: Re. 34,964

[45] Reissued Date of Patent: Jun. 13, 1995

[54] SHOCK WAVE TREATMENT APPARATUS

[75] Inventor: Kiyoshi Okazaki, Takanezawa, Japan

[73] Assignee: Kabushiki Kaisha Toshiba, Kawasaki, Japan

[21] Appl. No.: 87,354

[22] Filed: Jul. 8, 1993

Related U.S. Patent Documents

Reissue of:

[64] Patent No.: 4,962,754
Issued: Oct. 16, 1990
Appl. No.: 293,284
Filed: Jan. 4, 1989

U.S. Applications:

[63] Continuation of Ser. No. 821,744, Jan. 13, 1992, abandoned.

[30] Foreign Application Priority Data

Jan. 13, 1988 [JP] Japan ..... 63-3824
May 27, 1988 [JP] Japan ..... 63-129731

[51] Int. Cl.[6] ..... A61B 17/22

[52] U.S. Cl. ..... 128/660.03; 601/3; 601/4

[58] Field of Search ..... 128/660.03, 24 EL, 399; 607/97; 601/2, 3, 4

[56] References Cited

U.S. PATENT DOCUMENTS

| | | | |
|---|---|---|---|
| 4,305,296 | 12/1981 | Green et al. | 73/626 |
| 4,617,931 | 10/1986 | Dory | 128/660.03 |
| 4,741,008 | 4/1988 | Franke | 128/328 |
| 4,763,652 | 8/1988 | Brisson et al. | 128/24 A |
| 4,771,787 | 9/1988 | Wurster et al. | 128/660.03 |
| 4,803,995 | 2/1989 | Ishida et al. | 128/660.03 |
| 4,821,729 | 4/1989 | Makokski et al. | 128/660.03 |
| 4,917,095 | 4/1990 | Fry et al. | 128/24 EL |

FOREIGN PATENT DOCUMENTS

| | | |
|---|---|---|
| 0242511A1 | 10/1987 | European Pat. Off. . |
| 3426398C1 | 3/1986 | Germany . |
| 3543867A1 | 6/1987 | Germany . |
| 58-130034 | 8/1983 | Japan . |
| 62-49843 | 3/1987 | Japan . |

*Primary Examiner*—Ruth S. Smith
*Attorney, Agent, or Firm*—Finnegan, Henderson, Farabow, Garrett & Dunner

[57] ABSTRACT

A shock wave treatment apparatus has a shock wave applicator including a shock wave transducer for forming a focusing region of a shock wave for destroying an object to be destroyed in an object to be examined, and an ultrasonic transducer for transmitting/receiving an ultrasonic wave and acquiring ultrasonic tomographic image information. The shock wave applicator is aligned with the object to be destroyed, such that an overlap degree between a focusing region of the shock wave and the object to be destroyed is discriminated by an overlap degree discrimination circuit. When the calculation result of the overlap is smaller than a predetermined value, control is performed not to generate a shock wave. On the other hand, the shock wave application is mechanically aligned with the object, such that a support device supporting the applicator is operated so that a focal point position of the shock wave in the object to be examined can be moved to coincide with the object to be destroyed.

8 Claims, 6 Drawing Sheets

SHOCK WAVE TREATMENT APPARATUS

Matter enclosed in heavy brackets [ ] appears in the original patent but forms no part of this reissue specification; matter printed in italics indicates the additions made by reissue.

*This application is a continuation of application Ser. No. 07/821,744 filed Jan. 13, 1992, now abandoned.*

*This is an application for reissue of U.S. Pat. No. 4,962,754, issued Oct. 16, 1990 entitled "SHOCK WAVE TREATMENT APPARATUS".*

BACKGROUND OF THE INVENTION

1. Field of the Invention

The present invention relates to an improvement of a shock wave treatment apparatus for destroying an object, e.g., cancer cells, stone, in a subject to be examined by a focused energy of a shock wave, or to perform a treatment.

2. Description of the Related Art

A conventional shock wave treatment apparatus comprises a shock wave transducer for forming a shock wave focusing region (to be referred to as a focusing region hereinafter) for destroying an object in a subject to be examined, and an ultrasonic transducer for acquiring tomographic image information of the subject to be examined, although not particularly shown.

A tomographic image display unit displays a sound field region image in a so-called B mode based on the image information acquired by the ultrasonic transducer.

In the shock wave treatment apparatus with the above arrangement, an object to be destroyed, such as a stone, is set to fall within the focusing region. A shock wave is generated by the shock wave transducer, so that the shock wave of a high sound pressure is focused in the focusing region. Reflection of the shock wave occurs at a boundary between the object to be destroyed and living tissues due to a difference in acoustic impedanc between the object to be destroyed and the living tissues, thus causing an internal stress in the object to be destroyed. The internal stress destroys the object to be destroyed.

As described above, the object to be destroyed must fall within the focusing region. The object to be destroyed may be set to correctly fall within the focusing region at a given moment. However, when a shock wave is to be applied in practice, the object to be destroyed may be moved due to motion or breathing of the subject to be examined, and may fall outside the focusing region.

In this case, if a shock wave is generated, the object to be destroyed as a target cannot be destroyed. Normal living tissues do not cause large reflection of a shock wave, and hence, do not cause a permanent side effect. Nevertheless, a reflection-induced permanent side effect of a shock wave should be avoided. In practice, bleeding due to damaged capillaries frequently occurs upon a shock wave treatment. If the focusing region includes a portion having a large acoustic impedance, e.g., a bone, such a portion may be damaged.

In the conventional shock wave treatment apparatus, in order to avoid idle radiation of a shock wave accompanying such a danger, a variation in position of an object to be destroyed, e.g., a stone is estimated in synchronism with cardiac beats or breathing as described in an article "Japanese Patent Disclosure No. 58-130034, CB. Forsmann, Aug. 3, 1983)", and a shock wave is radiated.

In order to confirm that the object to be destroyed falls within the focusing region, a focal point marker indicating a vertex position of the focusing region is displayed on a sound field region image.

However, the prior art is based on merely estimation, and is not a reliable method for avoiding idle radiation of a shock wave.

That is, an object to be examined may sometimes undergo unexpected motion.

It is difficult for an operator to judge an overlap degree between the focusing region and the object to be destroyed within a short period of time by only display of the focal point marker. The above-mentioned prior art documents disclose no arrangement nor idea of controlling a shock wave applicator in consideration of a moving direction in an alignment operation for causing a focal point position of a shock wave to coincide with a stone or the like.

In addition, there are no known prior art documents which disclose a mechanical technique in which the moving direction of a shock wave applicator, in particular, an ultrasonic transducer as image information acquiring means is effectively regulated with respect to the present position of a stone.

SUMMARY OF THE INVENTION

The present invention has been made in consideration of the above situation, and has as its object to provide a shock wave treatment apparatus which can effectively perform alignment of an object to be destroyed in an object to be examined, and can shorten a time required from alignment to destruction.

In order to achieve the above object by electrical means, a shock wave treatment apparatus of the present invention for achieving the above object by electrical means, comprises:

shock wave generating means for forming a focusing region of a shock wave for destroying an object in a subject to be examined;

image information acquiring means, arranged within a shock wave transmission region of the shock wave generating means, for acquiring tomographic image information of the object to be examined;

overlap degree discriminating means for calculating an overlap degree between the focusing region of the shock wave and the object to be destroyed; and overlap degree variation information display means for displaying a variation in overlap degree obtained, with the passage of time, from the calculated result, and used an information for determining whether or not to generate shock waves.

In order to achieve the above object by mechanical means, a shock wave treatment apparatus of the present invention comprises:

shock wave applicator means including shock wave generating means for generating a shock wave focused in a subject to be examined so as to destroy an object in the subject to be examined, and image information acquiring means, arranged within a shock wave transmission region of the shock wave generating means, for acquiring tomographic image information of the subject to be examined; and support means for supporting the shock wave applicator so that a focal point position of the shock wave in the subject to be examined is movable.

With the above arrangement, the shock wave treatment apparatus of the present invention can determine an overlapping state between the object to be destroyed in the subject to be examined and the shock wave focusing region on a display screen, i.e., the positional relationship therebetween using the information-acquiring means. Thus, a time required for alignment and a time required for destruction can be shortened, and as a result, idle radiation of a shock wave can be avoided. Thus, a reliable and safe treatment can be achieved, and hence, a treatment time can be shortened. The shock wave treatment apparatus of the present invention can effectively perform alignment of the focal point position of the shock wave with respect to the object to be destroyed in the subject to be examined using the mechanical means, and hence, a destruction time can be shortened.

DETAILED DESCRIPTION OF THE PREFERRED EMBODIMENT

An embodiment of a shock wave treatment apparatus according to the present invention will now be described with reference to the accompanying drawings.

Figure 1:
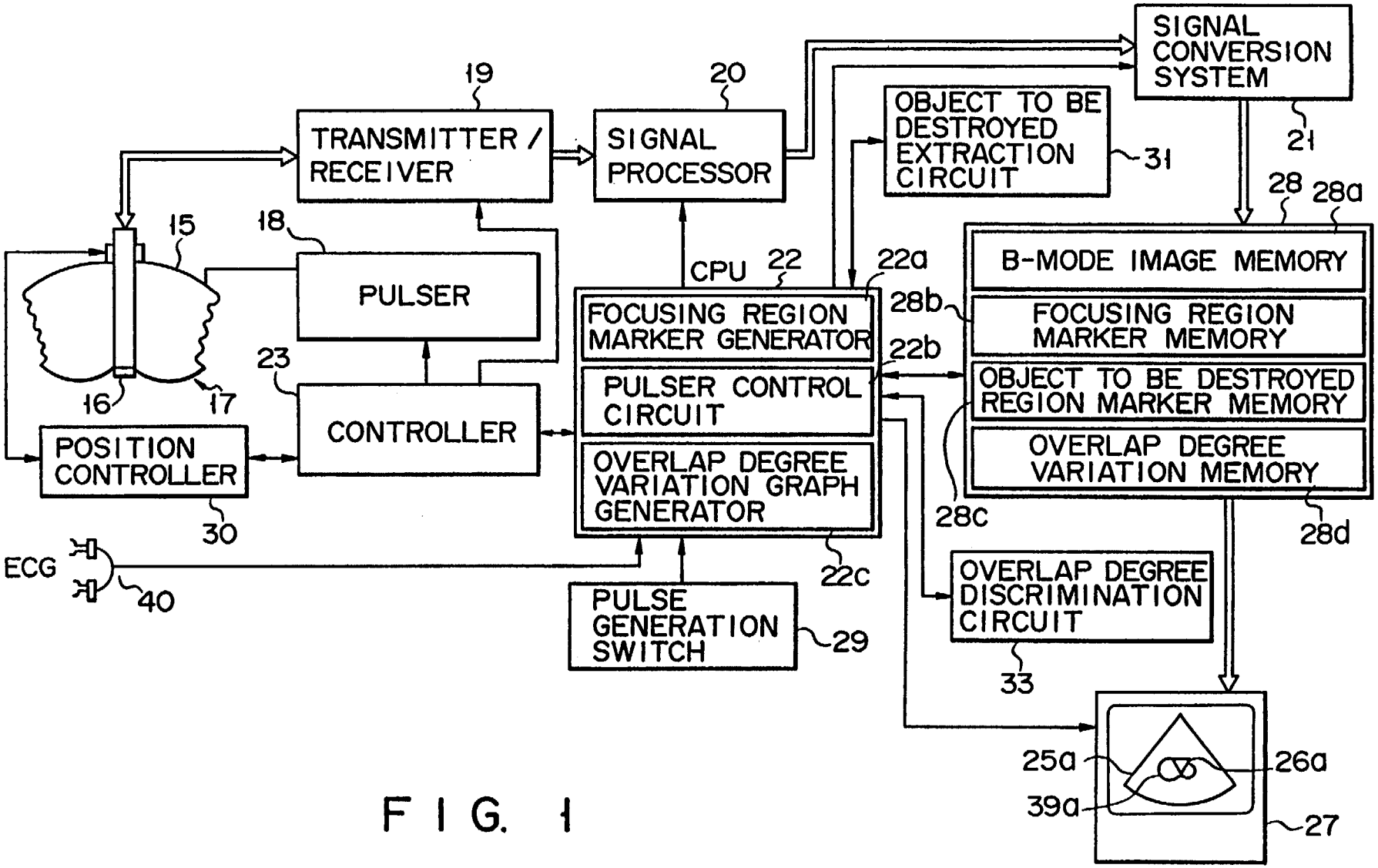
FIG. 1 is a block diagram showing an arrangement of a shock wave treatment apparatus according to the present invention.
Figure 2:
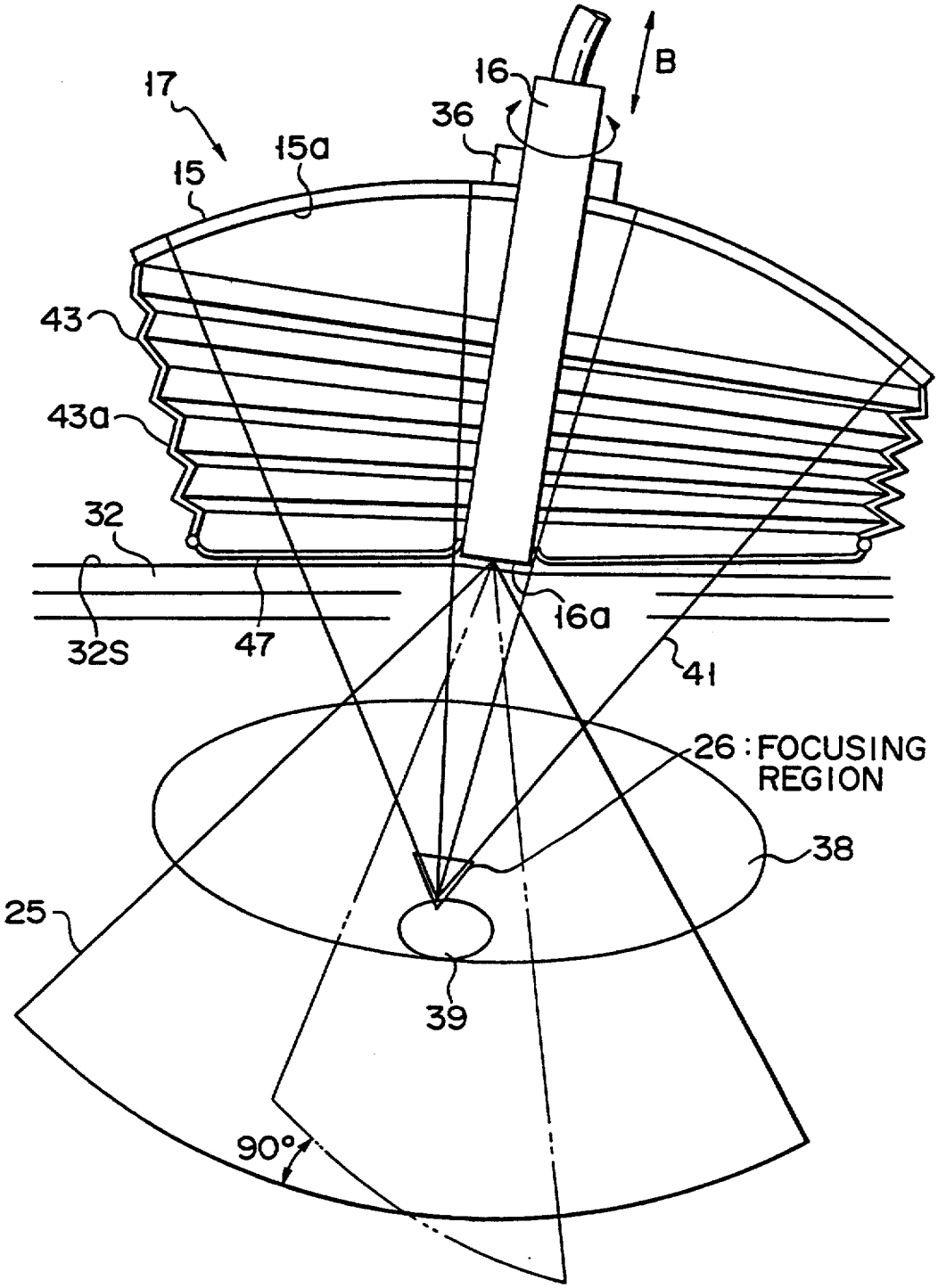
FIG. 2 is an explanatory view showing a section of an ultrasonic applicator as an embodiment of the shock wave treatment apparatus of the present invention, and a state in use of the applicator.

The shock wave treatment apparatus according to the present invention shown in FIG. 1 comprises shock wave applicator 17 including shock wave transducer 15 for forming a focusing region of a destruction shock wave of an object to be destroyed in [an] *a* subject to be examined, and ultrasonic transducer 16 for transmitting/receiving ultrasonic waves and acquiring ultrasonic tomographic information, pulser 18 for supplying a pulse signal to shock wave transducer 15, transmitter/receiver 19 for supplying a pulse signal to ultrasonic transducer 16, exciting ultrasonic transducer 16 to perform, e.g., a 4-stage focused sector scan of the well-known type shown, for example, in FIG. 2 of U.S. Pat. No. 4,305,296, and receiving an echo signal from ultrasonic transducer 16 upon each scan under the control of controller 23, signal processor 20 for receiving an output signal from transmitter/receiver 19, amplitude-detecting the input signal, and supplying the detected signal as a digital video signal to signal conversion system 21, central processing unit (CPU) 22 for performing control of the respective units of the apparatus, controller 23 for controlling transmission/reception timings, amplitude, frequency, and the like of the pulse signal in transmitter/receiver 19, signal processor 20, and pulser 18 under the control of CPU 22, signal conversion system 21, including a frame memory and line memory (not shown), performing signal conversion processing of an output signal of signal processor 20 under the control of CPU 22, TV monitor 27 for displaying focusing region marker 26a indicating a focusing region of a destruction shock wave sent from shock wave transducer 15 together with sector-shaped sound field region image 25a by ultrasonic transducer 16, kidney stone image 39a, based on the output signal from signal conversion system 21, image memory 28, pulse generation switch 29, connected to CPU 22 so as to set a generation timing of a pulse signal supplied from pulser 18 to the shock wave transducer 15, for indicating start of transmission of the pulse signal, position controller 30 for adjusting a positional relationship of ultrasonic transducer 16 relative to shock wave transducer 15, object to be destroyed extraction circuit 31, overlap degree discrimination circuit 33. Image memory 28 comprises B-mode image memory 28a, focusing region marker memory 28b, object to be destroyed region marker memory 28c, overlap degree variation memory 28d.

CPU 22 includes focusing region marker generator 22a comprising a predetermined program for displaying focusing region marker 26a at a position corresponding to a focusing region on a sound field region image, pulser control circuit 22b, comprising a predetermined program for comparing an overlap degree supplied from overlap degree discrimination circuit 33 and a preset value, for controlling the operation of shock wave pulser 18, and overlap degree variation graph generator 22c including a predetermined program for displaying an overlap degree variation graph.

In this embodiment, object to be destroyed extraction circuit 31 and overlap degree discrimination circuit 33 constitute overlap degree discrimination means, and pulser control circuit 22b corresponds to shock wave generation control means.

Shock wave applicator 17 in the shock wave treatment apparatus of the present invention will be described below with reference to FIG. 2.

In FIG. 2, shock wave applicator 17 has shock wave transducer 15 for forming focusing region 26 of a destruction shock wave (e.g., an ultrasonic wave pulse of a strong energy) for destroying an object to be destroyed, e.g., kidney stone 39 in the subject to be examined (or patient) 32, water bath 43 arranged on the side of ultrasonic wave transmission surface 15a of shock wave transducer 15, and ultrasonic transducer 16, arranged in shock wave transmission region 41 extending from shock wave transmission surface 15a of shock wave transducer 15 to focusing region 26, and forming sound field region 25 including focusing region 26 in a state wherein ultrasonic wave transmission/reception surface 16a is brought into contact with surface 32S of the patient, thereby acquiring tomographic image information of patient 32.

Shock wave transducer 15 comprises a concave vibrator having a predetermined curvature, and a backing member uniformly attached to the back surface of the vibrator (neither are shown). Ultrasonic transducer 16 is attached to the center of shock wave transducer 15 to be movable in directions of double-headed arrow B through transducer support/drive unit 36.

Transducer support/drive unit 36 comprises a mechanism capable of arbitrarily moving or stopping transducer 16 based on a control signal from position controller 30, a drive source therefor, and a position sensor for detecting the position of ultrasonic transducer 16 in the directions of arrow B.

Water bath 43 filled with water as a shock wave transmission liquid is arranged on the side of ultrasonic wave transmission surface 15a of shock wave transducer 15, as described above.

Water bath 43 shown in FIG. 2 has a cylindrical shape or frustum shape with a bottom having substantially the same outer dimensions as those of shock wave transducer 15. Bellows 43a which can be expanded/contracted in the directions of arrow B or within a predetermined angle from the direction is formed on the side surface of water bath 43. Bottom portion [47] *44* is formed of a thin film having an acoustic impedance substantially equal to that of water.

The function and effect of the shock wave treatment apparatus with the above arrangement will be explained while assuming a case wherein kidney stone 39 in kidney 38 shown in FIG. 2 is destroyed to perform a treatment.

Water bath 43 provided to shock wave applicator 17 is placed on surface 32S of patient 32. In this state, transmitter/receiver 19, signal processor 20, and signal conversion system 21 are controlled to drive ultrasonic transducer 16, so that a tomographic image from the patient is displayed on the screen of monitor 27.

In this case, focusing region marker generator 22a calculates, in real time, the present position of focusing region marker 26a on the screen based on B-direction deviation information of ultrasonic transducer 16 from transducer support/drive unit 36, and sequentially updates data in focusing region marker memory 28b for displaying the focusing region marker based on the calculation result, so that the present position is caused to correspond to memory data corresponding to the position, and focusing region marker 26a is displayed on monitor 27.

Sound field region image (B-mode image) 25a obtained by signal conversion system 21 is displayed to display an image of the object to be destroyed thereon. Since the object to be destroyed has a high acoustic impedance, it strongly reflects the ultrasonic wave, and is displayed in white relative to the surrounding living tissues on sound field region image 25a even without going through object to be destroyed extraction circuit 31.

In this embodiment, the sound field region image information is input to object to be destroyed extraction circuit 31 to extract and clarify the region of the object to be destroyed, and the extraction result is used in overlap degree discrimination later.

More specifically, this object to be destroyed extraction circuit 31 extracts pixels having brightness information exceeding a given value, and updates data in object to be destroyed region marker memory 28c through CPU 22 so that the extracted pixels are displayed in clear white.

Circuit 31 has a digital comparator, and performs the pixel extraction using the digital comparator.

Overlap degree discrimination circuit 33 receives information from CPU 22, and counts the number of extracted pixels included in focusing region marker 26a, and divides the count value with the total number of extracted pixels of the object to be destroyed, which are extracted by circuit 31, thus calculating an overlap degree.

An image is displayed on monitor 27 based on image information in the image memory generated as described above.

A displayed portion of a tomographic image of patient 32, which is displayed in real time, is changed upon movement of shock wave applicator 17.

When kidney stone image 39a is displayed in the tomographic image, shock wave applicator 17 is further finely adjusted, so that focusing region marker 26a coincides with kidney stone image 39a. In this state, shock wave applicator 17 is fixed.

Figure 3:
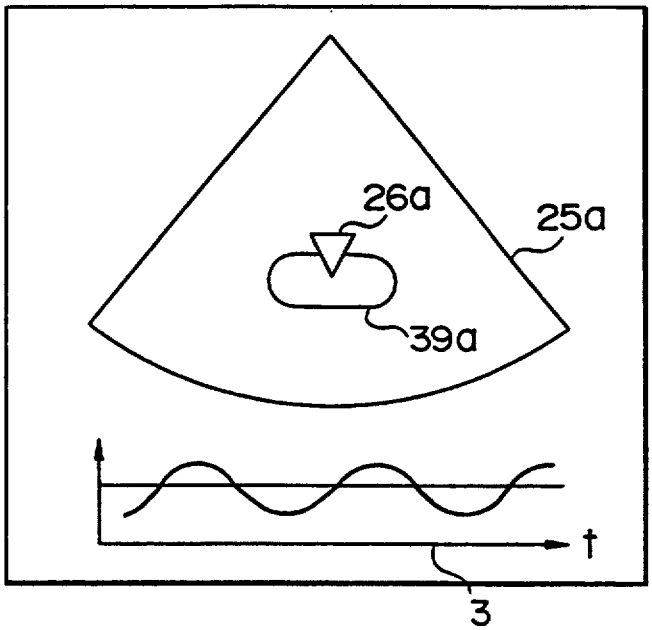
FIG. 3 is a view for explaining an overlap degree of a focusing region marker overlapping a B-mode image of an object to be destroyed in the embodiment of the present invention.

As shown in FIG. 3, an operator observes an image displayed on monitor 27. When he or she determines that focusing region marker 26a coincides with kidney stone image 39a and hence, kidney stone 39 falls in focusing region 26, he or she depresses pulse generation switch 29 to request generation of pulses.

However, in this case, an operation of pulse generation switch 29 may be delayed from perceptual determination of coincidence by the operator, and during this interval, the patient may move, or the operator may make an erroneous determination such that kidney stone 39 is not present in focusing region 26 or their images do not sufficiently overlap each other.

In this case, the following countermeasure is taken, and idle radiation of a shock wave can be avoided.

More specifically, the overlap degree when the pulse generation request is generated is compared with a predetermined reference value (10% in this embodiment) by pulser control circuit 22b in CPU 22. If it is determined that the calculated overlap degree is smaller than the reference value, pulser control circuit 22b controls not to generate the pulses at pulser 18. In this embodiment, the predetermined reference value is set to be 10%. However, the present invention is not limited to this.

If pulser control circuit 22b determines that the overlap degree is equal to or larger than the reference value, a pulse generation enable state is determined, and the pulse generation request is executed. A pulse signal is supplied from pulser 18 to shock wave transducer 15, and object to be destroyed 39 present in focusing region 26 in practice is destroyed by the strong shock wave.

In this embodiment, it can be determined in real time that an object to be destroyed is effectively included in the focusing region, and control for a pulse generation request is performed based on the determination result. Therefore, radiation of a shock wave can be reliably performed, and idle, dangerous radiation of a shock wave can be avoided.

A shock wave treatment apparatus according to another embodiment of the present invention will now be described.

FIG. 3 shows a display mode performed on a display unit in the shock wave treatment apparatus according to this embodiment. The shock wave treatment apparatus of this embodiment has substantially the same basic arrangement as that of the shock wave treatment apparatus of the above embodiment, except that CPU 22 further includes overlap degree variation graph generator 22c comprising a predetermined program for displaying an overlap degree variation graph, and image memory 28 includes overlap degree variation memory 28d. Controller 23 includes trigger pulse generating means (although not shown). The same reference numerals in this embodiment denote the same parts as in the above embodiment.

Overlap degree variation graph generator 22c, overlap degree variation memory 28d, and the like correspond to overlap degree variation information display means.

In the shock wave treatment apparatus of this embodiment, overlap degree discrimination circuit 33 calculates an overlap degree as an integral value of brightness of a B-mode image included in focusing region marker 26a.

More specifically, the position of focusing region marker 26a on the B-mode image 25a is calculated from the information from position control 30. The brightnesses of pixels of the B-mode image of focusing region marker 26a are read out from B-mode image memory 28a based on the position of focusing region marker 26a, and a sum of them is calculated. The sum serves as the overlap degree.

In this embodiment, the overlap degree is obtained by a simple arrangement, and high-speed signal processing is allowed.

Overlap degree variation graph generator 22c plots the overlap degrees from the present value to, typically, a value 5 seconds before the present time, which are successively supplied from overlap degree discrimination circuit 33 to CPU 22 on monitor 27 as overlap degree variation graph 3. This display can be achieved by updating data in overlap degree variation memory 28d by overlap degree variation graph generator 22c.

Figure 4:
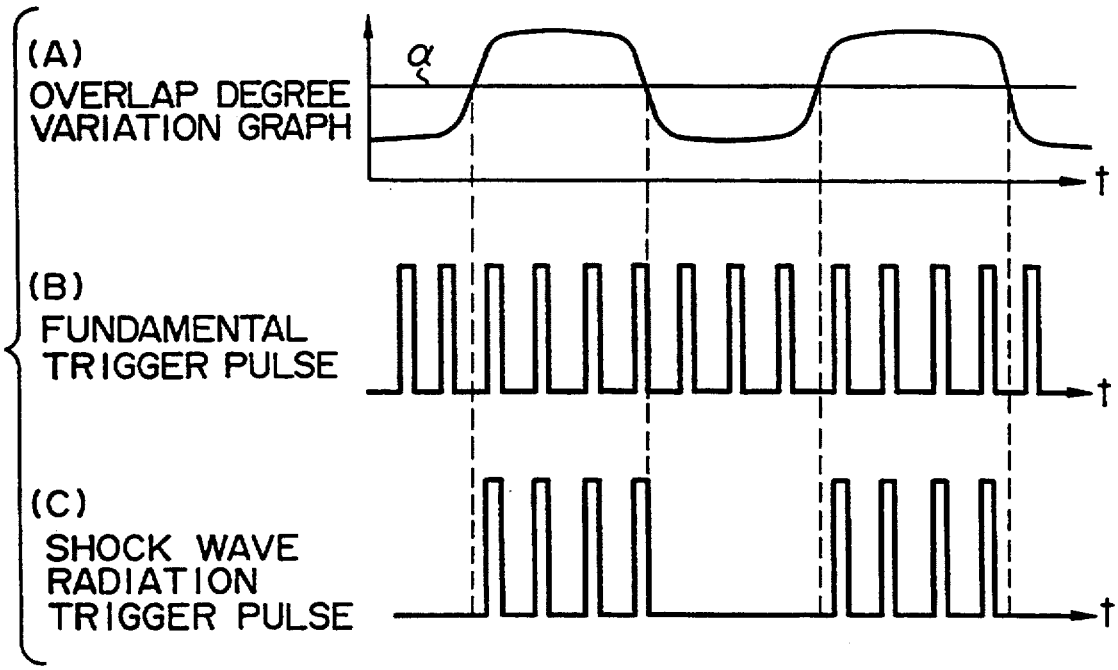
FIGS. 4A to 4C are timing charts showing modes of a variation in overlap degree and corresponding generation timings of a shock wave.

FIG. 4A illustrates a case wherein the overlap degree almost periodically changes about reference value $\alpha$ by mainly breathing of a patient. In this embodiment, the reference value of the overlap degree is set to be 10%.

Since a variation in overlap degree over time can be displayed on the screen, an operator can properly determine the overlapping state between the kidney stone and the focusing region, and can predict a change in overlap degree after the present time. These are very difficult to achieve when only a focal point marker is displayed on a B-mode image, and can be easily achieved only by displaying the overlap degree variation graph as in this embodiment.

When the operator turns on pulse generation switch 29, pulser control circuit 22b in CPU 22 discriminates if the overlap degree at that time exceeds reference value $\alpha$. Only when pulser control circuit 22b determines that the overlap degree exceeds reference value $\alpha$, it controls pulser 18 through controller 23 so that pulse radiation is performed when trigger pulses are input from controller 23 to pulser 18.

FIG. 4B shows a case wherein five trigger pulses per second are generated by the trigger pulse generating means. This frequency can be varied within the range of 2 to 10 pulses per second.

When the overlap degree is varied, as shown in FIG. 4A, a shock wave is generated in response to the trigger pulses shown in FIG. 4C.

The operator confirms that the stone is destroyed by a series of radiation of pulses while observing the green, and can turn off pulse generation switch 29, so that pulse radiation can be immediately stopped.

As can be seen from the above embodiment, the shock wave treatment apparatus of the present invention can provide the following effects.

More specifically, since a mode of a variation in overlap degree can be displayed, the overlapping state between the object to be destroyed and the focusing region or the positional relationship therebetween can be easily determined, idle radiation of a shock wave can be avoided, and a reliable and safe treatment can be performed.

Whether or not the object to be destroyed is effectively included in the focusing region of the shock wave is discriminated, and execution of the pulse generation request is controlled based on the discrimination result. If it is determined that the object to be destroyed is not effectively included in the focusing region, the radiation of the shock wave is stopped. Therefore, idle radiation of the shock wave can be avoided, a reliable and safe treatment can be performed; and as a result, a treatment time can be shortened.

Another embodiment will be described below. In this embodiment, the shock wave applicator in the shock wave treatment apparatus of the present invention is provided with a support device, and is movably supported by the support device, so that a focal point of a shock wave in a patient can be easily and quickly aligned with an object to be destroyed by mechanical means, resulting in a decrease in a destruction time.

Figure 5:
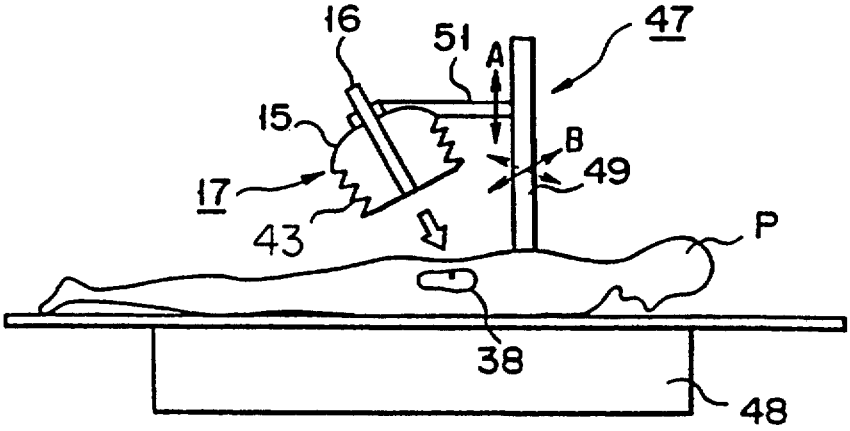
FIG. 5 is a view showing a state wherein the shock wave applicator is movably supported on a support device.
Figure 6:
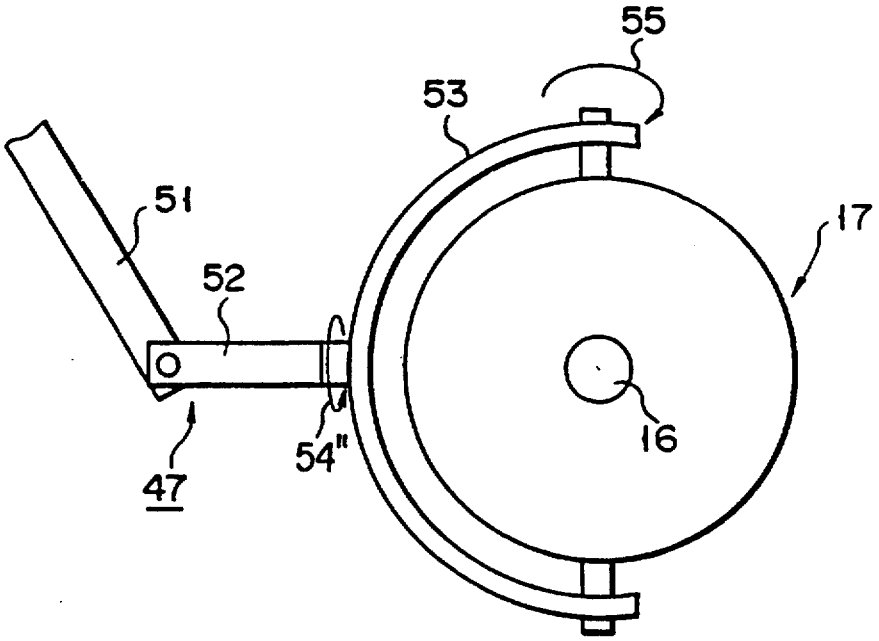
FIG. 6 is a top view of the shock wave applicator for explaining a pivotal state of the support device shown in FIG. 5.

Destruction shock wave applicator 17 shown in FIG. 2 is supported by applicator support device 47, as shown in FIG. 5. Applicator support device 47 supports the applicator so that applicator 17 is pivotal about the distal end portion (in this case, a wave transmission/-reception surface of an ultrasonic probe) of ultrasonic transducer 16, and a distance between shock wave transducer 15 and an object to be destroyed (in this case, a kidney stone 39 present in kidney 38 of patient P) can be adjusted by motions yielding appropriate degrees of freedom, e.g., motion A and/or either B of two such orthogonal motions in FIG. 5. FIG. 6 is a top view of shock wave applicator 17 and applicator support device 47. First arm 51 is mounted on column 49 shown in FIG. 5, and one end of second arm 52 is pivotally supported on the other end of first arm 51. The central portion of arcuated third arm 53 is pivotally supported on the other end of second arm 52 for pivotal motion 54'' about arm 52; and applicator 17 is supported at two end portions of third arm 53 to be pivotal in a direction indicated by arrow 55.

The operation of the apparatus of this embodiment with the above arrangement will be described while assuming a case wherein kidney stone 39 in kidney 38 shown in FIG. 2 is destroyed.

The procedure of focal point alignment of a shock wave will be described below with reference to FIGS. 7 to 9.

Figure 8:
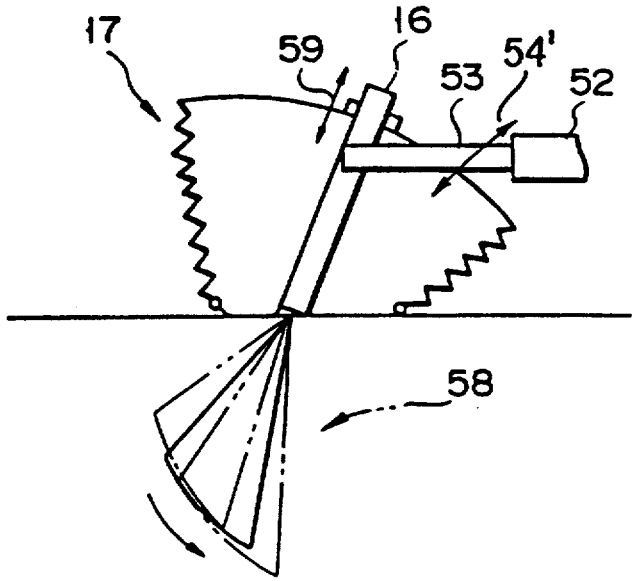
FIG. 8 is a view for explaining an operation for causing the shock wave applicator shown in FIG. 7 to perform a second swing.
Figure 9:
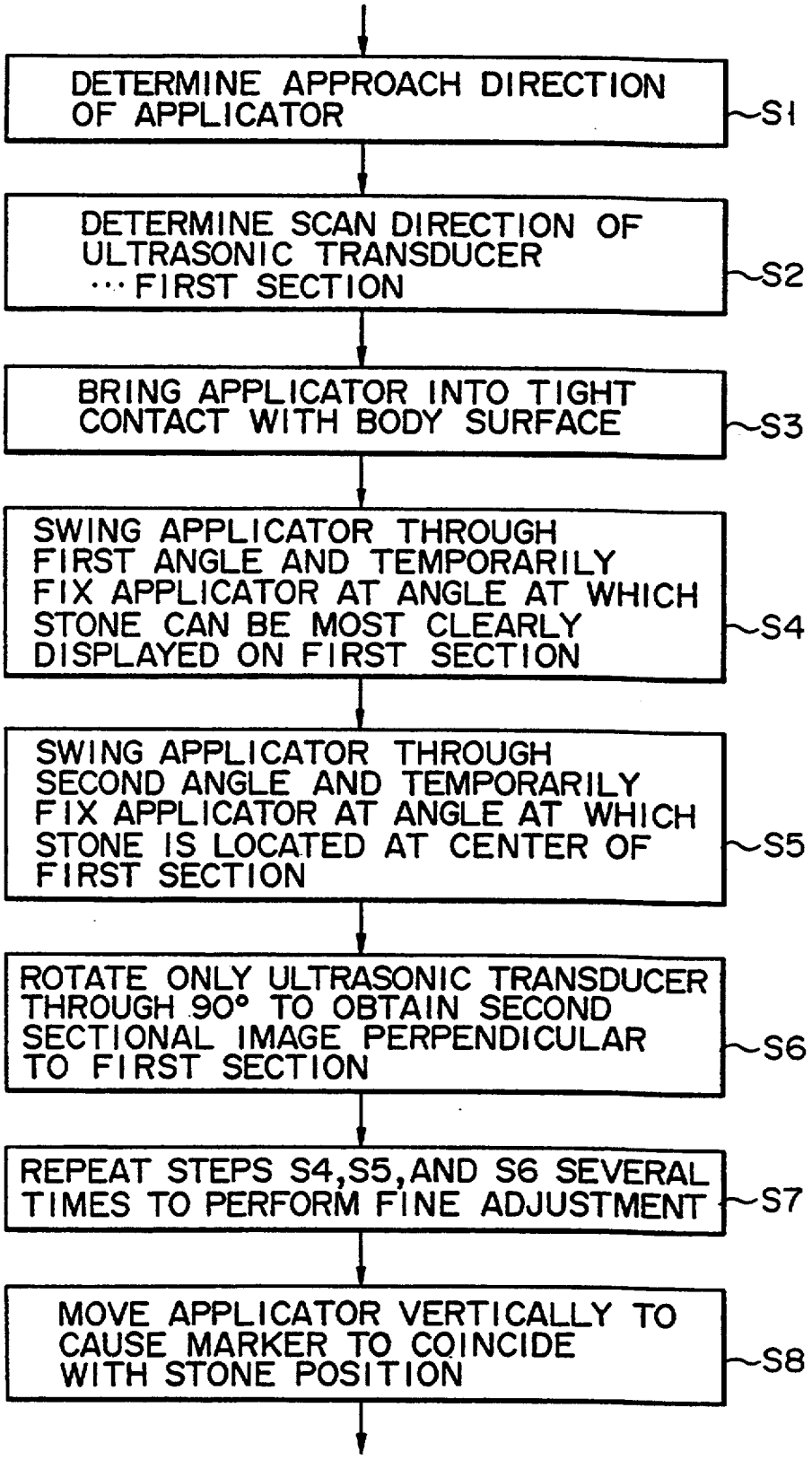
FIG. 9 is a flow chart of an alignment operation of a focal point of a shock wave.

When shock wave applicator 17 is directed to patient P, the approach direction of applicator 17 is determined (S1), as shown in step S1 in the flow chart of FIG. 9, and the scan direction of ultrasonic transducer 16 is determined (S2). See also FIGS. 5, 7 and 8. In this case, the scan direction is determined so as to determine whether a longitudinal section of patient P parallel to the body axis of patient P is to be scanned or his or her cross-section is to be scanned, and can be arbitrarily determined by the operator. A section specified by determination of the scan direction is given by a first section. For the purpose of descriptive simplicity of the embodiment shown in FIG. 7, the first section is assumed to be a cross-section.

Shock wave applicator 17 is brought into tight contact with the body surface of patient P (S3). Image information of patient P is acquired by ultrasonic transducer 16 under the control of controller 23. The acquired image information is visualized by TV monitor 27. The operator swings shock wave applicator 17 through a first angle while observing the display image, and temporarily fixes applicator 17, for example, by a well-known electromagnetic brake, at an angle at which kidney stone 39 can be most clearly displayed in this cross-section (S4). The swing movement of applicator 17 through the first angle is achieved by pivoting applicator 17 in a direction of arrow 54 in FIG. 7 about the distal end portion (ultrasonic wave transmission/reception surface 16a) of ultrasonic transducer 16. The movement in this case is performed by pushing or pulling second arm 52. With this pivotal movement, a plurality of different B-mode images (tomographic images) 57 in the first section of patient P are sequentially displayed on TV monitor 27 shown in FIG. 1, as shown in FIG. 7. Therefore, shock wave applicator 17 can be easily temporarily fixed at an angle at which kidney stone 39 is most clearly displayed.

In this state, shock wave applicator 17 is swung through a second angle, and is temporarily fixed at the angle a which the image of kidney stone 39 is located at the center of the first section (S5). The swing movement of shock wave applicator 17 through the second angle is performed by pivoting applicator 17 in a direction of arrow 55 in FIG. 6 about the distal end portion of ultrasonic transducer 16. In this case, this operation can be performed by pushing or pulling first arm 51.

Figure 7:
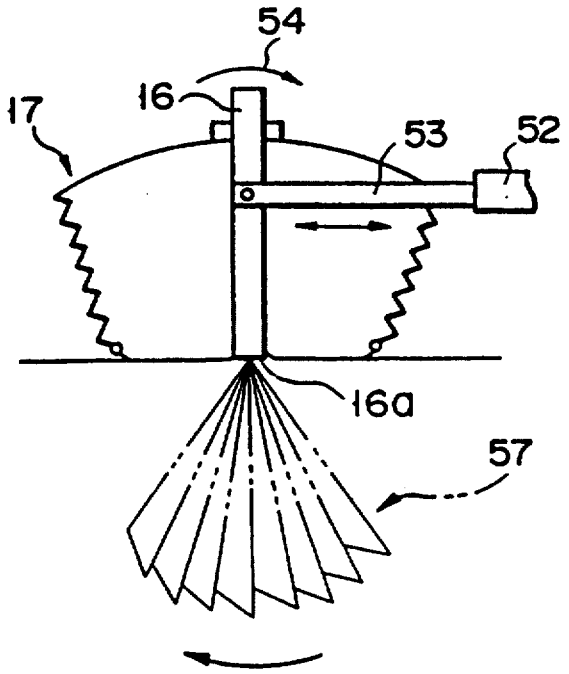
FIG. 7 is a view for explaining an operation for causing the shock wave applicator to perform a first swing so as to align the focal point of a shock wave.

As shown in FIG. 2, only ultrasonic transducer 16 is rotated through 90° about its axis, and a plurality of second sectional images 58, i.e., longitudinal sectional images perpendicular to the first section, e.g., the cross-section are obtained, as shown in FIG. 8 by rotation of transducer 16 and arm 53 through an arc 54' orthogonal to arc 54 of FIG. 7. Note that since patient P moves, steps S2, S3, and S4 are repeated to perform fine adjustment (S7). If temporarily fixing in step S5 is appropriately performed, the image of the kidney stone should be displayed at the center of the display screen in both the first and second sections. In this manner, kidney stone 39 can be three-dimensionally displayed by the respective displays of the perpendicular sections discussed above with respect to FIGS. 7 and 8.

Focusing region marker 26 indicating a geometrical focusing region of a shock wave transmitted from shock wave transducer 15 is displayed on monitor 27, and the operator moves shock wave [applicator 17] *transducer 15* in the direction of arrow B while observing the image displayed on monitor 27, thereby adjusting the distance between shock wave transducer 15 and kidney stone 39 and causing focusing region marker 26 to coincide with kidney stone 39. In this case, ultrasonic transducer 16 is not moved but is fixed in position.

In this manner, the focal point alignment of the shock wave can be completed.

The operator then operates a first switch of pulse generation switch 29, and supplies a control signal to pulser 18 through CPU 22 and controller 23. A shock wave signal is transmitted from pulser 18 to shock wave transducer 15. Shock wave transducer 15 transmits a shock wave of strong energy to kidney stone 39 present at a position corresponding to focusing region marker 26.

The shock wave is repetitively transmitted as needed, thereby destroying entire kidney stone 39.

Shock wave transducer 15 of this embodiment is formed into a spherical shape to have a predetermined curvature, and has a coil which is helically wound about the axis of ultrasonic transducer 16, and a metal film which is laminated on the coil through an insulating member, thus constituting a single electromagnetic induction type sound source. A plurality of electromagnetic induction type sound sources may be juxtaposed, or a concave ultrasonic vibrator may be used.

Note that since a patient slightly moves due to cardiac beats and breathing, living body signal detector 40 may be brought into contact with the hand, leg, chest, nose, or the like of the patient in advance. The living body signal obtained by living body signal detector 40 is synchronized with a signal from pulse generation switch 29 by CPU 22, thereby controlling a transmission timing of the pulse signal from pulser 18.

In the apparatus of this embodiment, since the position of shock wave applicator 17 is determined based on image information of orthogonal sections (first and second sections) in a patient, appropriate focal point alignment can be achieved. Therefore, a kidney stone as an object to be destroyed can be effectively destroyed, and a destruction time can be shortened.

The present invention is not limited to the above embodiment, and various other changes and modifications may be made within the spirit and scope of the invention.

According to the embodiment described above, since appropriate focal point alignment can be achieved by the mechanical means, a time required for destroying an object to be destroyed present in a patient can be shortened.

What is claimed is:

1. A shock wave treatment apparatus comprising:

shock wave generating means for forming a focusing region of a destruction shock wave for destroying an object in a subject to be examined;

image information acquiring means, arranged in a shock wave transmission region of said shock wave generating means, for acquiring tomographic image information of the subject to be examined and the object to be destroyed;

overlap degree discriminating means for calculating an overlap degree between said focusing region of the shock wave and the object to be destroyed; and overlap degree variation information display means for displaying a variation in overlap degree obtained, with the passage of time, from the calculated result, and used as information for determining whether or not to generate shock waves by said shock wave generating means.

2. An apparatus according to claim 1, wherein said overlap degree discriminating means comprises means for extracting object information and means for determining the overlap degree.

3. An apparatus according to claim 1, wherein said overlap degree variation information display means comprises an overlap degree variation graph generator and an overlap degree variation memory.

4. A shock wave treatment apparatus comprising:

shock wave generating means for forming a focusing region of a destruction shock wave for destroying an object in a subject to be examined;

image information acquiring means, arranged in a shock wave transmission region of said shock wave generating means for acquiring tomographic image information of the object to be destroyed;

overlap degree discrimination means for calculating an overlap degree between the focusing region of the destruction shock wave and the object to be destroyed;

shock wave generation control means for inhibiting generation of the shock wave when the calculation result of the overlap degree obtained by said overlap degree discrimination means is smaller than a predetermined value; and display means for displaying a tomographic image of the object to be examined and destroyed, said tomographic image being derived from said tomographic image information.

5. An apparatus according to claim 4, wherein said overlap degree discrimination means comprises means for extracting object information and means for discriminating overlap degree.

6. A shock wave treatment apparatus comprising:

shock wave applicator means including shock wave generating means for generating a shock wave focused in an object to be destroyed in a subject to be examined, and image information acquiring means, arranged within a shock wave transmission region of said shock wave generating means, for acquiring tomographic image information of the object to be destroyed;

support means for supporting said shock wave applicator means so that a focal point position of the shock wave in the subject to be examined is movable;

overlap degree discrimination means for calculating an overlap degree between the focusing region of the destruction shock wave and the object to be destroyed;

shock wave generation control means for controlling the generation of the shock wave, to inhibit said generation when the overlap degree obtained by said overlap degree discrimination means is smaller than a predetermined value;

wherein said shock wave applicator support means supports said shock wave applicator means so that said shock wave applicator means is pivotal about a distal end portion of said image information acquiring means and a distance between said shock wave generating means and the object to be destroyed can be adjusted.

7. An apparatus according to claim 6, wherein said image information acquiring means can acquire a plurality of pieces of image information in orthogonal sections of the subject to be examined.

*8. A shock wave treatment apparatus comprising:*

*shock wave applicator means including: (i) shock wave generating means for generating a shock wave focused in an object to be destroyed in a subject to be examined, and (ii) image information acquiring means arranged within a shock wave transmission region of said shock wave generating means to acquire tomographic image information on the object to be destroyed and designed to acquire two tomographic images from respective planes of the object that are perpendicular to each other;*

*and support means for supporting said shock wave applicator means,*

*said support means rendering said shock wave applicator means pivotable about a distal end portion of the image information acquiring means, rotatable about two mutually perpendicular axes, and movable in three mutually perpendicular directions, whereby the spacing between the shock wave generating means and the object is adjustable, and*

*the shock wave generating means being movable forward and backward longitudinally along the image information acquiring means to further adjust the spacing between the shock wave generating means and the object,*

*the two tomographic images corresponding to two of the three mutually perpendicular directions.*

* * * * *